(12) United States Patent
Sharma

(10) Patent No.: US 12,390,224 B2
(45) Date of Patent: Aug. 19, 2025

(54) STEERABLE PLATFORM REPOSITIONABLE OVER THE SCOPE CLIP

(71) Applicant: BOSTON SCIENTIFIC MEDICAL DEVICE LIMITED, Galway (IE)

(72) Inventor: Deepak Kumar Sharma, Muzaffarnagar (IN)

(73) Assignee: Boston Scientific Medical Device Limited, Galway (IE)

( * ) Notice: Subject to any disclaimer, the term of this patent is extended or adjusted under 35 U.S.C. 154(b) by 431 days.

(21) Appl. No.: 18/053,606

(22) Filed: Nov. 8, 2022

(65) Prior Publication Data

US 2023/0225740 A1    Jul. 20, 2023

Related U.S. Application Data

(60) Provisional application No. 63/266,807, filed on Jan. 14, 2022.

(51) Int. Cl.
*A61B 17/12*    (2006.01)
*A61B 17/122*   (2006.01)
*A61B 17/128*   (2006.01)

(52) U.S. Cl.
CPC ........ *A61B 17/1285* (2013.01); *A61B 17/122* (2013.01)

(58) Field of Classification Search
CPC ... A61B 17/0682; A61B 17/083; A61B 17/10; A61B 17/122; A61B 2017/00323
See application file for complete search history.

(56) References Cited

U.S. PATENT DOCUMENTS

| | | | |
|---|---|---|---|
| 9,138,227 B2 | 9/2015 | Schostek et al. | |
| 2002/0062130 A1 | 5/2002 | Jugenheimer et al. | |
| 2005/0187613 A1* | 8/2005 | Bolduc | A61B 17/115 623/1.23 |
| 2009/0065549 A1* | 3/2009 | Viola | A61B 17/072 606/205 |

(Continued)

FOREIGN PATENT DOCUMENTS

| | | |
|---|---|---|
| EP | 2 403 421 | 7/2019 |
| WO | 2010/104755 | 9/2010 |

*Primary Examiner* — Alexander J Orkin
(74) *Attorney, Agent, or Firm* — Fay Kaplun & Marcin, LLP

(57) ABSTRACT

A clipping system for treating tissue including an adapter, a clip, an extending member and a control wire. The adapter couplable to an insertion device via steering members. The steering members extend alongside the insertion device and connect to the adapter to steer the adapter between a first position and a second position. The clip mounted over the adapter. The clip includes first and second jaws connected to one another and movable between an insertion configuration and an initial deployed configuration. The extending member slidably received within one of the steering members. The control wire slidably received within the extending member and extends through the first jaw such that simultaneous longitudinal movement of the control wire and the extending member relative to the adapter moves the clip between the insertion configuration, the initial deployed configuration, and a review configuration in which the clip is separated from the adapter.

15 Claims, 8 Drawing Sheets

(56) References Cited

U.S. PATENT DOCUMENTS

| | | | |
|---|---|---|---|
| 2011/0152888 A1* | 6/2011 | Ho | A61B 1/00087 |
| | | | 606/151 |
| 2011/0282176 A1 | 11/2011 | Tegg | |
| 2015/0257757 A1* | 9/2015 | Powers | A61B 17/1285 |
| | | | 606/142 |
| 2017/0135693 A1* | 5/2017 | Cardinale | A61B 17/068 |
| 2020/0397445 A1* | 12/2020 | Shikhman | A61B 17/083 |
| 2020/0397455 A1 | 12/2020 | Shikhman et al. | |
| 2021/0059677 A1* | 3/2021 | Jin | A61B 17/122 |
| 2021/0235969 A1 | 8/2021 | Solano Montenegro et al. | |

* cited by examiner

STEERABLE PLATFORM REPOSITIONABLE OVER THE SCOPE CLIP

PRIOR CLAIM

The present disclosure claims priority to U.S. Provisional Patent Application Ser. No. 63/266,807 filed Jan. 14, 2022; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks). Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient.

In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed. Once deployed, such current over-the scope clips are generally incapable of being repositioned.

SUMMARY

The present disclosure relates to a clipping system for treating tissue including an adapter, a clip, a first extending member and a first control wire. The adapter includes a proximal portion configured to be coupled to a distal end of an insertion device via steering members extending from proximal ends to distal ends. The steering members extends alongside the insertion device with distal ends of the steering members connected to the proximal end of the adapter so that moving the steering members longitudinally relative to the insertion device steers the adapter between a first position, in which the adapter is substantially aligned with a longitudinal axis of the insertion device, and a second position, in which the adapter is angled away from the longitudinal axis of the insertion device. The clip is mounted over a distal portion of the adapter. The clip includes first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween. The first and second jaws are biased toward the initial deployed configuration. The first extending member is slidably received within one of the steering members so that a distal end of the first extending member extends distally toward the clip. The first control wire is slidably received within the first extending member and through an opening extending through the first jaw of the clip so that an enlarged distal end of the first control wire extends distally of the opening, the enlarged distal end of the first control wire and the distal end of the first extending member being sized, shaped and configured such that the clip is held therebetween so that a simultaneous longitudinal movement of the first control wire and the first extending member relative to the adapter moves the clip between the insertion configuration, the initial deployed configuration, and a review configuration in which the clip is physically separated from the adapter to enhance visual observation of the clip.

In an embodiment, the enlarged distal end of the first control wire is connected to a remaining length thereof via a joint configured to separate the enlarged distal end from the remaining length when subject to a force exceeding a predetermined threshold value.

In an embodiment, each of the enlarged distal end of the first control wire and the distal end of the first extending member has a cross-sectional area that is larger than a cross-sectional area of the opening of the first jaw.

In an embodiment, the proximal portion of the adapter includes a first hole extending longitudinally through a wall thereof to slidably receive the first extending member therein such that the distal end of the first extending member extends distally of the first hole toward the clip.

In an embodiment, the system further includes a second extending member received slidably through another one of the steering members so that a distal end of the second extending member extends distally toward the clip; and a second control wire slidably received within the second extending member and through an opening extending through the second jaw of the clip so that an enlarged distal end of the second control wire extends distally of the opening of the second jaw, the enlarged distal end of the second control wire and the distal end of the second extending member being sized, shaped and configured such that the clip is held therebetween and a simultaneous longitudinal movement of the second control wire and the second extending member relative to the adapter moves the clip between the insertion configuration, the initial deployed configuration, and the review configuration.

In an embodiment, the system further includes outer shafts extending alongside the insertion device from proximal ends to distal ends, each of the outer shafts configured to slidably house a corresponding one of the steering members therein.

In an embodiment, each of the steering members is configured as a hollow braided pebax.

In an embodiment, each of the steering members includes at least two steering wires extending longitudinally through a wall thereof.

The present disclosure relates to a clipping system for treating tissue. The system includes an endoscope extending longitudinally from a proximal end to a distal end; an adapter including a proximal portion and a distal portion, the proximal portion configured to be mountable over the distal end of the endoscope and connected thereto via first and second steering members extending from proximal ends to distal ends, the steering members extending alongside the endoscope with distal ends of the steering members connected to the proximal end of the adapter so that moving the steering members longitudinally relative to the endoscope steers the adapter between a first position, in which the adapter is substantially aligned with a longitudinal axis of the endoscope, and a second position, in which the adapter is angled away from the longitudinal axis of the endoscope; a clip configured to be mounted over the distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration; first and second extending members, each of the first and second extending member extending longitudinally through a corresponding one of the first and second steering members so that distal ends of the first and second extending members extend through the proximal portion of the adapter distally toward the clip; and first and second control wires, each of the first and second control wires slidably received within a corresponding one of the first and second extending members and through an opening extending through a corresponding one of the first and second jaws of the clip so that an enlarged distal end of the first and second control wire extend distally of the openings, the enlarged distal ends of the first and second control wire and the distal ends of the first and second extending members being sized, shaped and configured such that the clip is held therebetween, and a simultaneous longitudinal movement of the first control wire and the first extending member relative to the adapter moves the clip between the insertion configuration, the initial deployed configuration, and a review configuration in which the clip is physically separated from the adapter to enhance a visual observation of the clip.

In an embodiment, each of the enlarged distal ends of the first and second control wires is connected to a remaining length thereof via a joint configured to separate the enlarged distal ends from the remaining lengths when subject to a force exceeding a predetermined threshold value.

In an embodiment, the enlarged distal ends of the first and second control wires and the distal ends of the first and second extending members have a cross-sectional area that is larger than a cross-sectional area of the openings of the jaws.

In an embodiment, the system further includes outer shafts extending alongside an insertion device from proximal ends to distal ends, each of the outer shafts configured to slidably house a corresponding one of the steering members therein.

In an embodiment, the system further includes a user interface including a first actuator configured to control a longitudinal movement of the first and second steering members relative to the endoscope, a second actuator configured to control a longitudinal movement of the first and second extending members relative to the adapter, and a third actuator configured to control a longitudinal movement of the first and second control members relative to the adapter.

In an embodiment, the user interface further includes a locking mechanism locking the second and third actuators relative to one another such that actuation of one of the second and third actuators simultaneously moves the first and second extending members along with the first and second control wires in the same longitudinal direction relative to the adapter.

In an embodiment, the user interface further includes a locking mechanism configured to lock the second actuator relative to the endoscope so that the third actuator is actuatable to move the first and second control wires relative to the first and second extending members and the endoscope to cause the joint to separate.

In addition, the present disclosure relates to a method for treating tissue. The method includes inserting a clip to a target area in a body lumen via an endoscope, the clip mounted over a distal end of the endoscope, via an adapter, in an open insertion configuration in which jaws of the clip are separated from one another; drawing tissue into a channel of the adapter and between jaws of the clip; moving the clip from the open insertion configuration toward an initial deployed configuration by releasing a tension along a control wire, the clip held between an enlarged distal end of the control wire and a distal end of an extending member so that a simultaneous distal longitudinal movement of the control wire and the extending member relative to the adapter permits the jaws to revert to a biased closed configuration, in which the jaws extend toward one another to grip the tissue received therebetween; and drawing the endoscope proximally away from the clip, while the clip remains held between the distal ends of the control wire and the extending member, toward a review configuration in which a visualization of the clip via the endoscope is enhanced.

In an embodiment, steering the adapter between a first position, in which the adapter is substantially longitudinally aligned with the endoscope, and a second position, in which the adapter is angled away from a longitudinal axis of the endoscope, via steering members connecting the adapter to the endoscope to further enhance a visibility.

In an embodiment, when it is determined that the clip requires repositioning, simultaneously moving the control wire and the extending member proximally relative to the endoscope until the clip is drawn proximally over the adapter toward the open insertion configuration and repositioning the clip over the target tissue.

In an embodiment, the method further includes moving the clip from the review configuration toward a final deployed configuration by drawing the control wire proximally relative to the extending member so that the enlarged distal end is pulled against the distal end of the extending member until a force exerted thereon exceeds a predetermined threshold force, separating the enlarged distal end of the control wire from a remaining length thereof to release the clip from the endoscope.

In an embodiment, the method further includes locking a movement of the control wire relative to the extending member to facilitate a simultaneous longitudinal movement of the control wire and the extending member relative to the endoscope.

BRIEF DESCRIPTION

DETAILED DESCRIPTION

Figure 1:
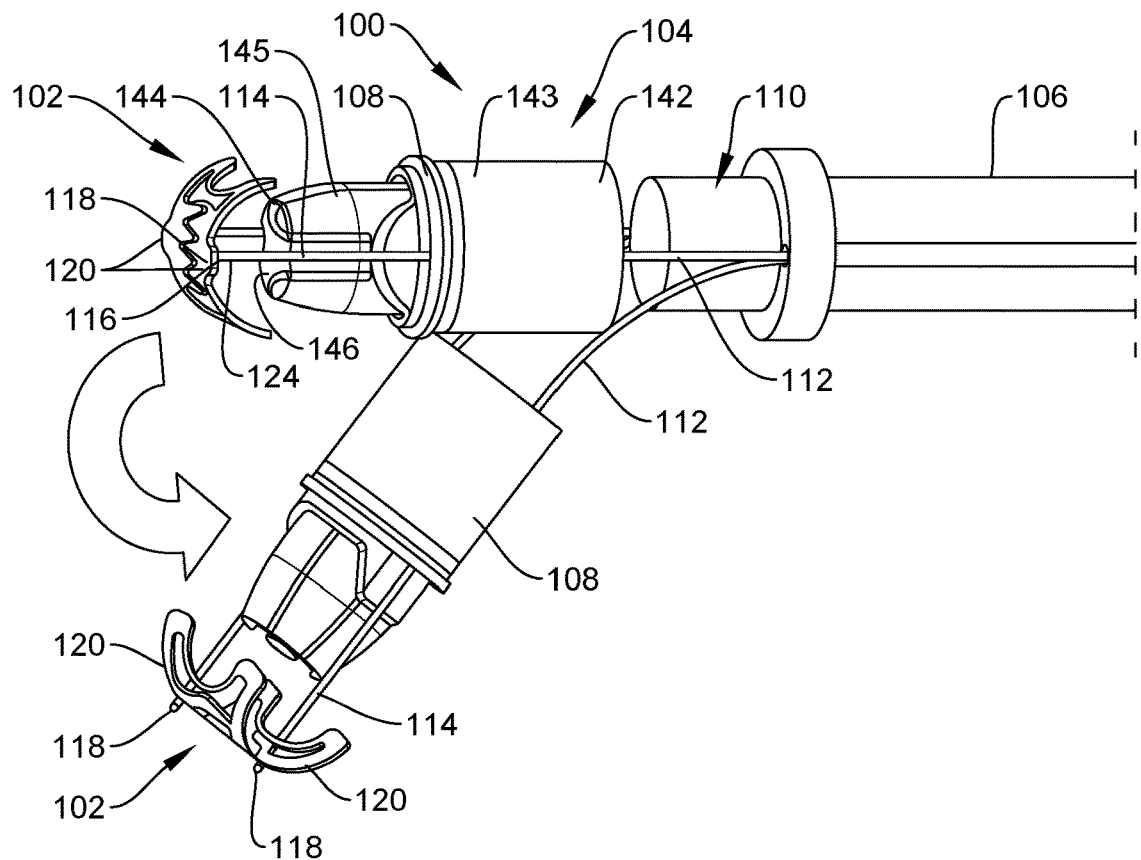
FIG. 1 shows a perspective view of a distal portion of a system according to an exemplary embodiment of the present disclosure, an adapter of the distal portion steerable from a first position to a second position.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to the final deployment thereof. Exemplary embodiments of the present disclosure comprise a clip mountable over a distal end of an endoscope via an adapter.

According to an exemplary embodiment, the adapter is coupled to the distal end of the endoscope via steering members, which enable movement of the adapter relative to the endoscope. In one embodiment, the steering members are configured to steer the adapter relative to the endoscope by, for example, angling the adapter away from a longitudinal axis of the endoscope to improve control and visualization via the endoscopic vision system. The clip is mountable over the adapter and is releasably coupled to extending members so that the clip may be moved relative to the adapter between an insertion configuration, an initial deployed configuration, and a review configuration, in which the clip can be viewed prior to being finally deployed. The steering members may be used to move (e.g., steer) the adapter relative to the endoscope during any of the insertion configuration, the initial deployed configuration, and the review configuration.

In the insertion configuration, the clip is mounted over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope to be withdrawn proximally away from the clip and the tissue over which it is clipped while the clip remains coupled to the device in a review configuration.

As the endoscope is withdrawn proximally while the clip remains in place over the target tissue, the field of view of the vision system of the endoscope widens to show the clip and the tissue clipped thereby so that the operator can determine whether the position of the clip is desirable or in need of adjustment. If the operator determines that the clip is positioned as desired, the clip is deployed by releasing the clip from the clasps of the extending members and left in place clipped over the target tissue. If the operator determines that the position of the clip needs adjustment, the endoscope and the adapter coupled thereto are moved distally to a position adjacent to the clip. The clip is then drawn proximally over the adapter to reopen the clip which is drawn proximally over the distal end of the adapter forcing the clip to open against its natural bias as the clip slides proximally back over the adapter to return to the insertion configuration.

After the clip has been removed from the tissue and returned to the insertion configuration, the operator can re-position the endoscope and device as desired, draw target tissue into the adapter (e.g., under suction or a grasper applied via a working channel of the endoscope) and once more deploy the clip from the adapter over the target tissue in the initial deployed position. The endoscope is then withdrawn proximally once again as the clip remains coupled to the device so that the device moves again into the review configuration. The position of the clip and the clipped tissue are again observed and, this process may be repeated until the clip is positioned as desired. When the operator sees that the tissue over which the clip is closed is the desired portion of tissue, the clip may be released from the extending members to be moved toward the final deployed configuration. It will be understood by those of skill in the art that terms proximal and distal, as used herein, are intended to refer to a direction toward and away from, respectively, a user of the device.

As shown in FIGS. 1-12, a clipping system 100 for treating tissue defects and/or perforations according to an exemplary embodiment comprises a clip 102 configured to be inserted through, for example, a body lumen to a target area to clip a target tissue thereof. The clip 102 is insertable to the target area via an insertion device 104 including, for example, an endoscope 106 and an adapter 108, which couples the clip 102 to a distal end 110 of the endoscope 106. The adapter 108 is coupled to the distal end 110 of the endoscope 106 via steering members 112, which facilitate movement of the adapter relative to the endoscope between a first position and a second position, as shown in FIG. 1.

In the first position the adapter 108 may be substantially aligned relative to the endoscope 106 while in a second position the adapter 108 may be angled or bent away from a longitudinal axis of the endoscope 106. The clip 102 is mountable over a portion of the adapter 108 and is movable relative to the endoscope 106 via extending members 114, to which the clip 102 is releasably coupled via control wires 116. Each of the control wires 116 extends through a corresponding one of the extending members 114 and includes an enlarged distal end 118 that is configured to be releasably engaged with a portion of a corresponding jaw 120 of the clip 102 to, together with the extending members 114, facilitate movement of the clip 102 relative to the endoscope 106 between an insertion configuration, an initial deployed configuration, a review configuration, and a final deployed configuration.

According to one embodiment, the enlarged distal end 118 of each of the control wires 116 is configured to engage an opening 122 extending through a corresponding one of the jaws 120. The openings 122 of this embodiment are sized and shaped to prevent passage of the enlarged distal ends 118 therethrough. Thus, when the enlarged distal ends 118 of the control wires 116 are positioned distally of the clip 102 and distal ends 124 of the extending members 114 are positioned proximally of the clip 102, the clip 102 is held between the distal ends 118, 124 of the control wires 116 and the extending members 114 so that a simultaneous motion of the control wires 116 and the extending members 114 relative to the adapter 108 controls movement of the clip 102 between the insertion configuration, the initial deployed configuration and the review configuration, as will be described in further detail below.

Figure 2:
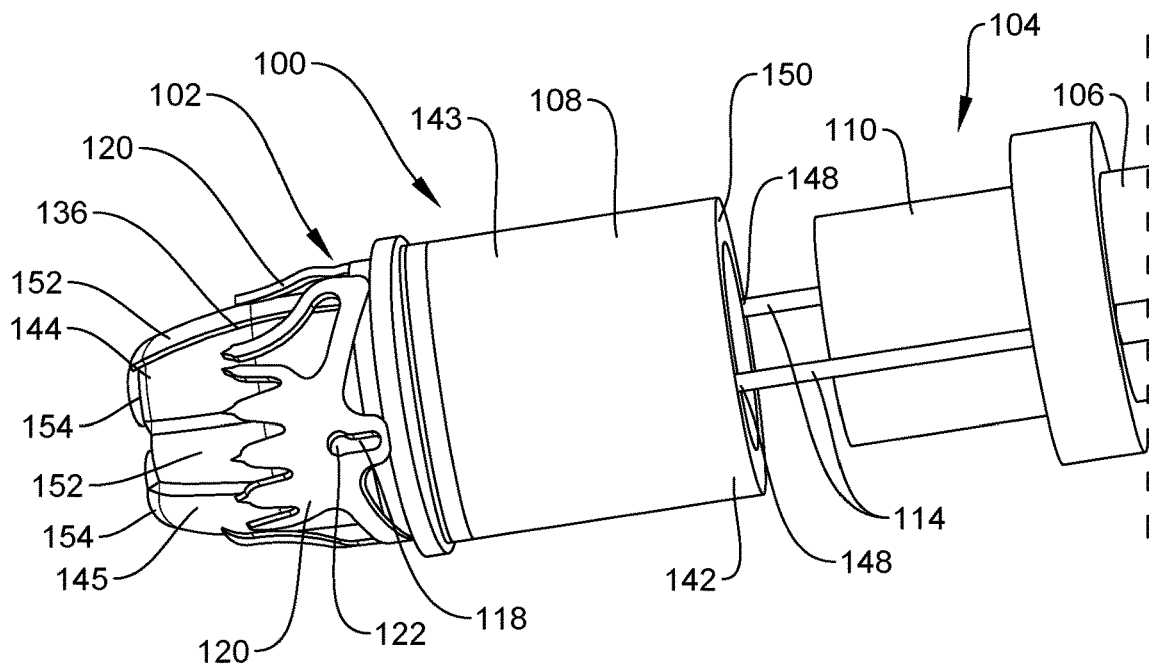
FIG. 2 shows a longitudinal side view of the distal portion of the system according to FIG. 1, with a clip of the system in an insertion configuration.

In the insertion configuration, as shown in FIG. 2, the clip 102 is mounted over the adapter 108 with jaws 120 of the clip 102 separated from one another to receive tissue that is drawn therebetween. To move the clip 102 from the insertion configuration toward the deployed configuration, the extending members 114 and the control wires 116 are moved distally relative to the adapter 108 and/or the endoscope 106, permitting the clip 102 to be moved distally off of the adapter 108 toward a closed configuration, in which the jaw 120 are moved toward one another to grip tissue that has been drawn into the adapter 108.

Figure 3:
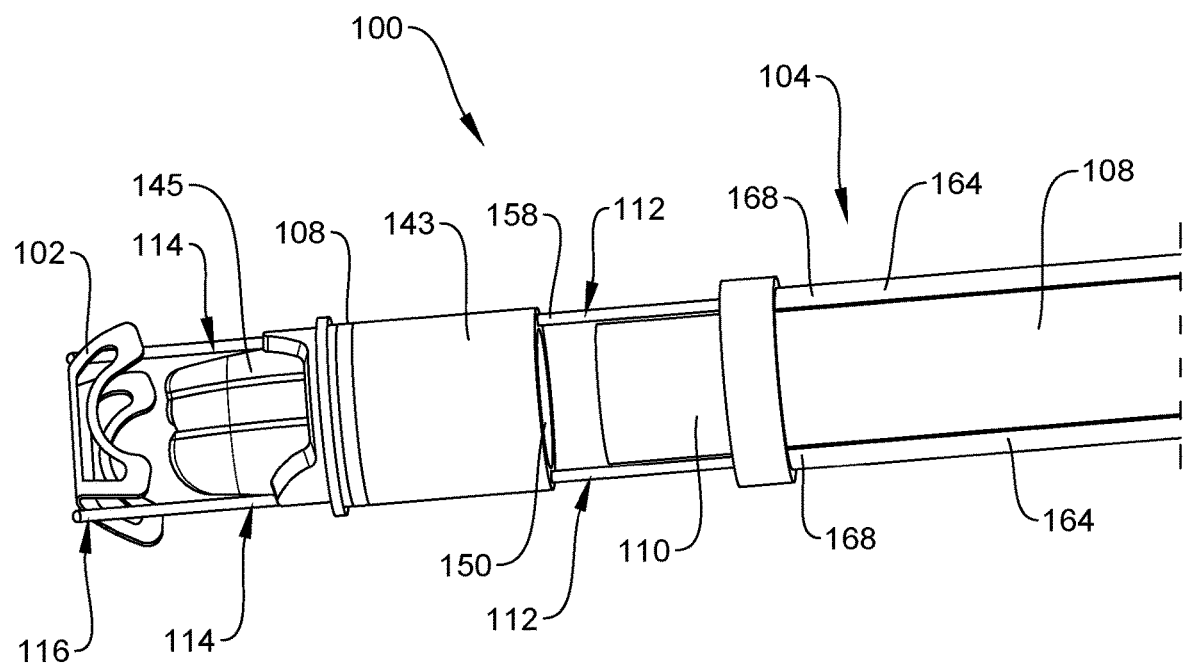
FIG. 3 shows a longitudinal side view of the distal portion of the system according to FIG. 1, with the clip of the system in the review configuration and the adapter in the first position.

Upon clipping of the tissue via the jaws 120 in the initial deployed configuration, the clip 102 is moved toward the review configuration, as shown in FIG. 3, by moving the extending members 114 and the control wires 116 distally away from the endoscope 106 (or drawing the endoscope 106 proximally relative to the extending members 114 and control wires 116) so that the clip 102 is distanced from the adapter 108, while remaining tethered to the insertion device 104 via the extending members 114 and the control wires 116. This widens the field of view of the endoscope vision system relative to the clip 102 and the target tissue and allows for some movement of the endoscope 106 relative to the clip 102 to enable more extensive observation of the placement and/or position of the clip 102 relative to the target tissue.

As described below, if the user determines the position of the clip 102 is incorrect or sub-optimal, the user may move the endoscope 106 distally to a position adjacent to the clip 102 and then retract the clip 102 back over the distal end of the adapter 108 to re-open the clip 102 and release any clipped tissue (i.e., to move the clip 102 back toward the open insertion configuration). The user may then reposition the endoscope 106 and the clip 102 and repeat these steps so that the placement and/or position of the clip 102 relative to target tissue may be adjusted, as desired, prior to a final deployment of the clip 102. That is, if the operator determines in the review configuration that the clip 102 is not positioned as desired (i.e., that tissue has not been clipped as desired or that a desired portion of tissue to be clipped has not been clipped as desired), the clip 102 may be re-opened and removed from the tissue so that the device can be re-positioned until the clip 102 is closed over the desired portion of tissue.

Figure 4:
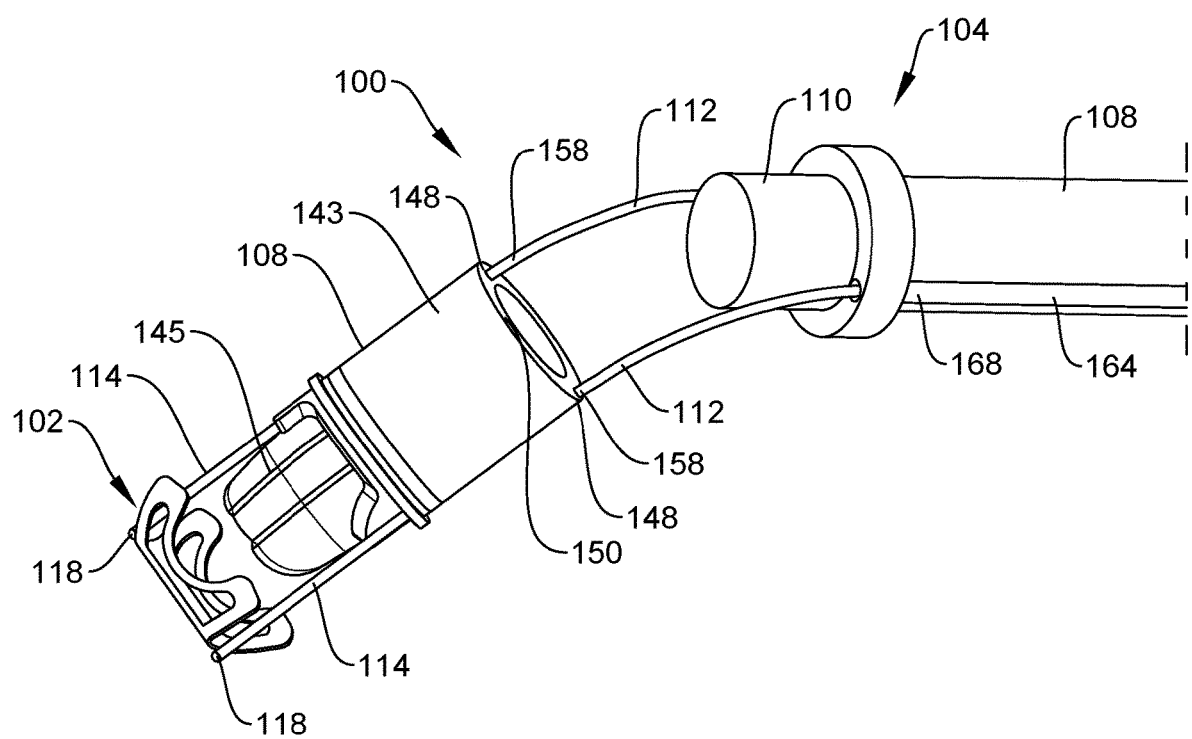
FIG. 4 shows a perspective view of the distal portion of the system according to FIG. 1, with the adapter moved toward the second position.

During any of the insertion configuration, the initial deployed configuration and the review configuration, the user may move the adapter 108 relative to the endoscope 106 via the steering members 112 to control and/or enhance a visualization of the clip 102 and/or tissue. It will be understood by those of skill in the art, however, that it may be particularly useful to steer the adapter 108 relative to the endoscope 106 during the review configuration, as shown in FIG. 4, to better confirm whether the desired tissue has been clipped. As will be described in further detail below, once it is determined that the clip 102 has been clipped over the desired tissue, the control wires 116 may be drawn proximally relative to the extending members 114 until the enlarged distal ends 118 are pulled against the clip 102.

Figure 11:
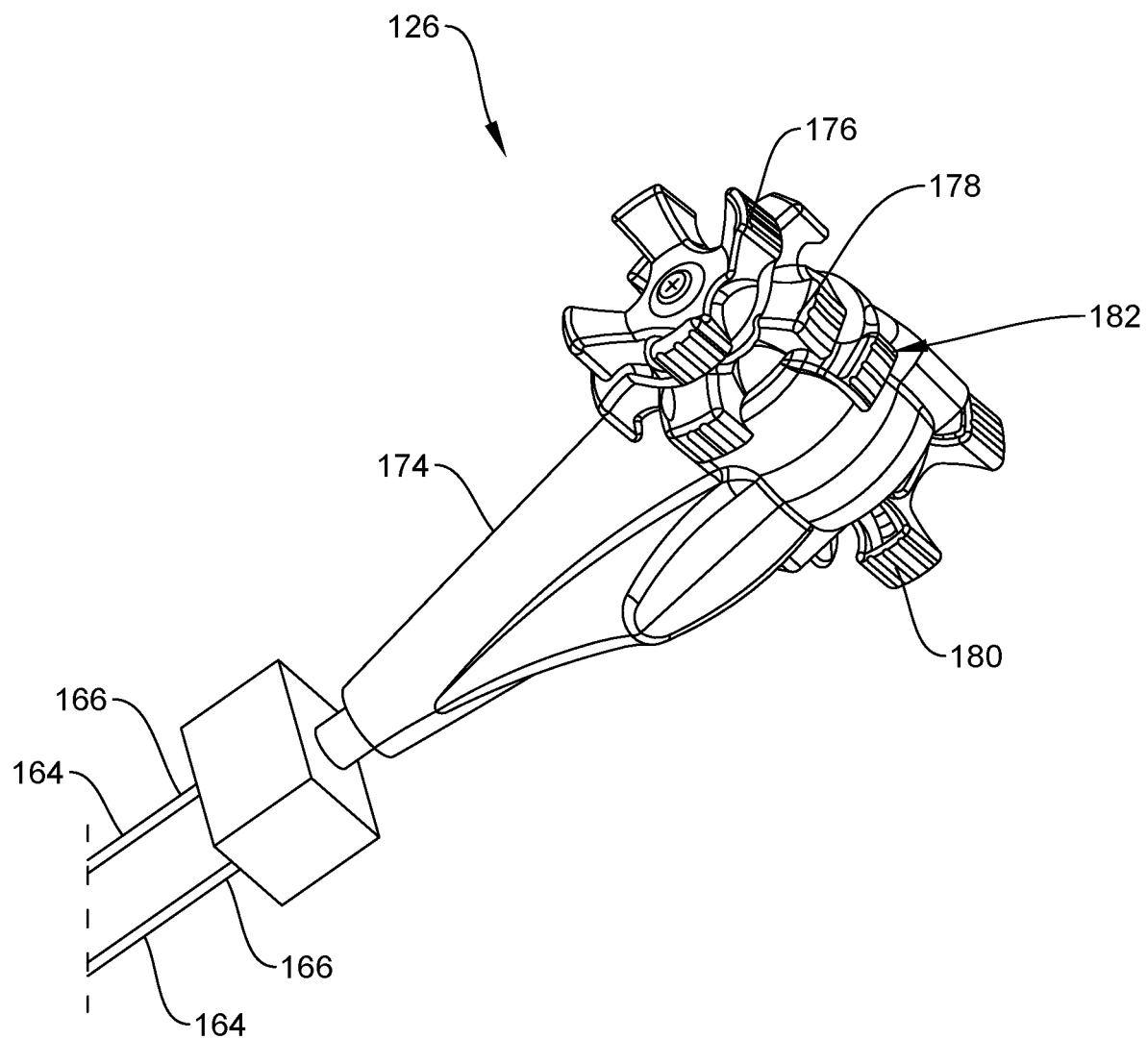
FIG. 11 shows a perspective view of a user interface according to the system of FIG. 1.
Figure 12:
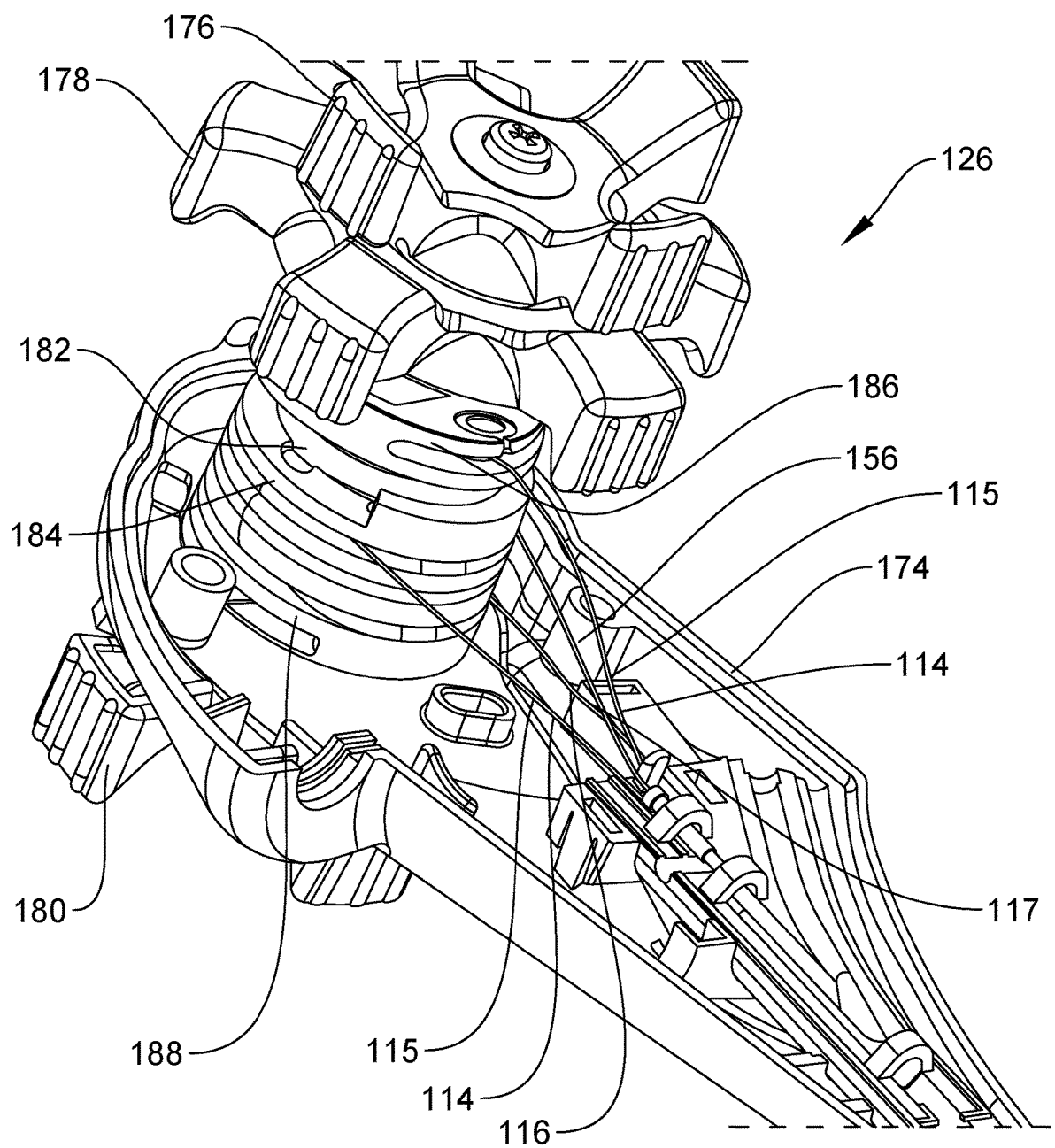
FIG. 12 shows a cross-sectional perspective view of the user interface according to the system of FIG. 1.
Figure 13:
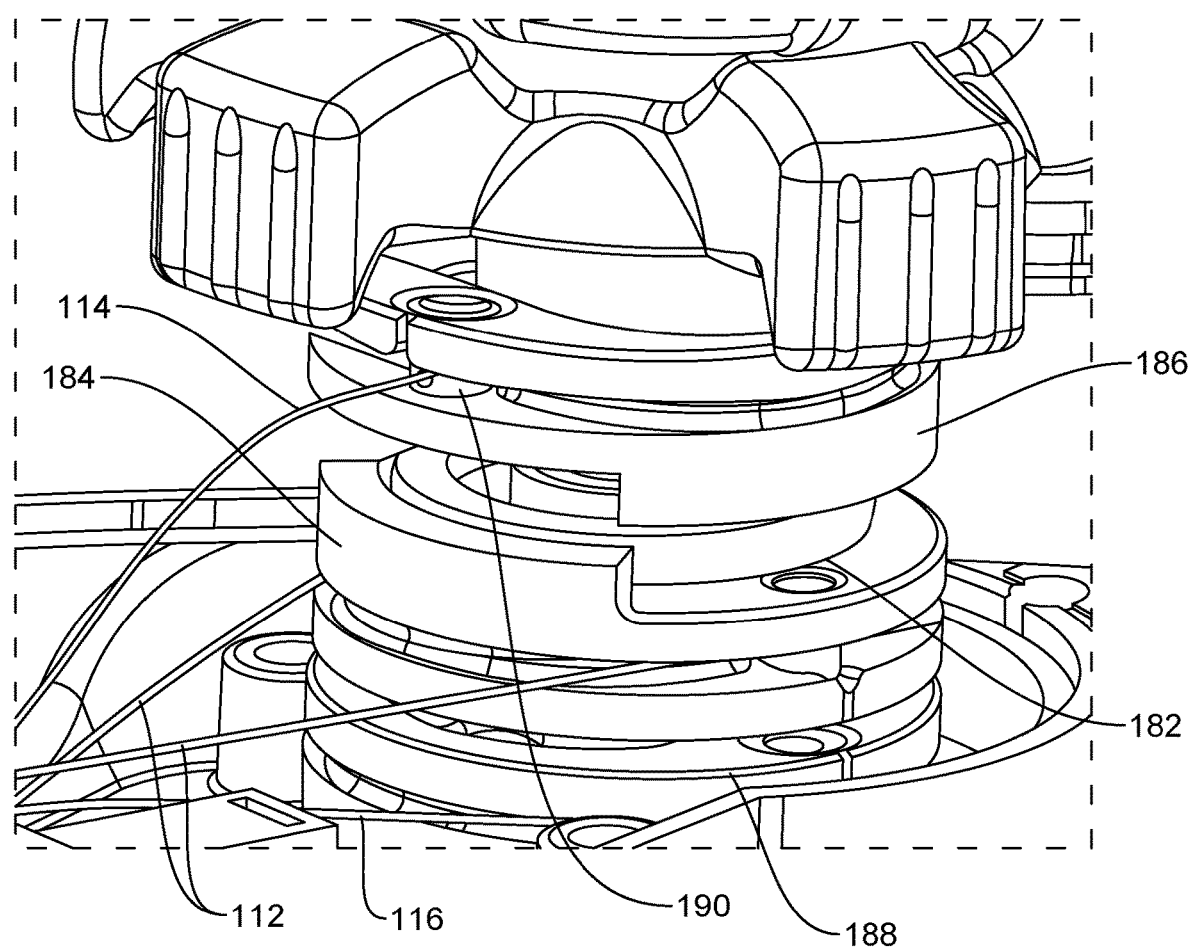
FIG. 13 shows an enlarged side view of the user interface according to the system of FIG. 1.

When a predetermined threshold force is exerted on the enlarged distal ends 118, the enlarged distal ends 118 are separated from a remaining length of the control wires 116, to release the clip 102 from the insertion device 104 deploying the clip 102 in the body. As will be understood by those of skill in the art and as will be described in further detail below, actuation of each of the steering members 112, extending members 114 and the control wires 116 to control the movement of the clip 102 between the insertion configuration, the initial deployed configuration, the review configuration and the final deployed configuration may be controlled via a user interface 126 which, in one embodiment, as shown in FIGS. 11-13, is coupled to a proximal end of the endoscope 106.

Figure 5:
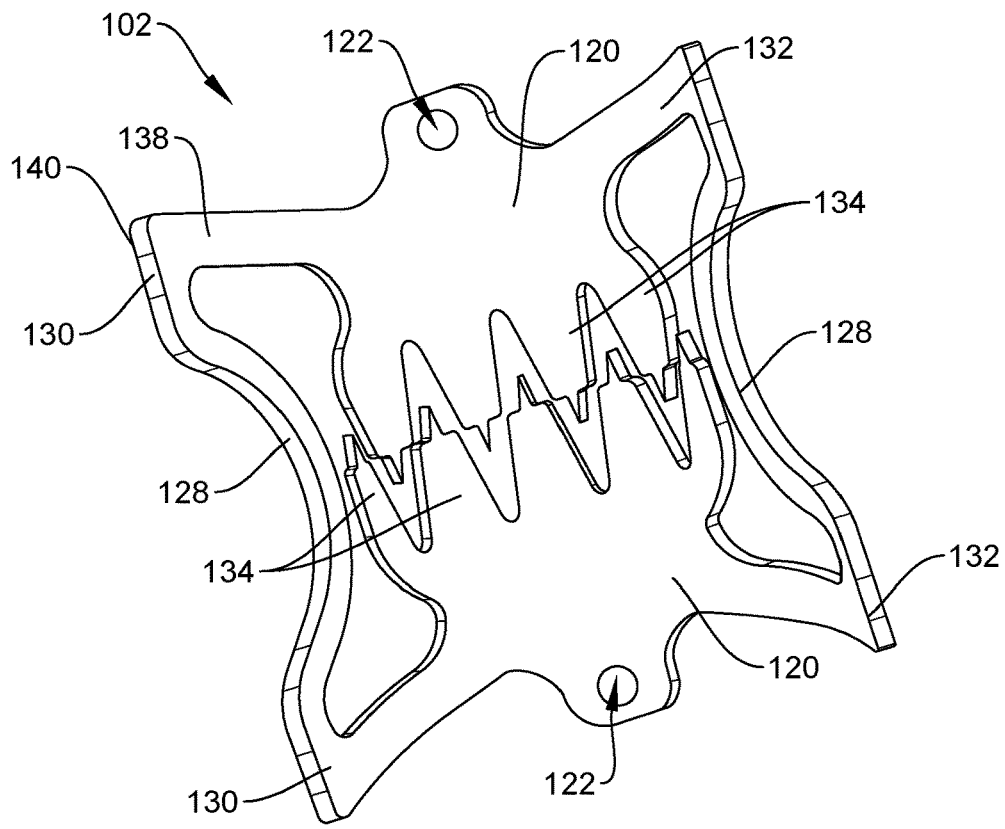
FIG. 5 shows a side view of the clip according to the system of FIG. 1.

As shown in FIG. 5, the clip 102 includes a pair of jaws 120 connected to one another via hinges 128. In one embodiment, each of the jaws 120 extends along a curve from a first end 130 to a second end 132 so that a first one of the hinges 128 connects the first ends 130 of each of the jaws 120 to one another, while a second one of the hinges 128 connects the second ends 132 of each of the jaws 120 to one another. In one embodiment, the hinges 128 are spring biased, biasing the jaws 120 toward the initial deployed configuration in which the jaws 120 are moved toward one another, in a closed configuration. Each of the jaws 120 of this embodiment includes one or more gripping features 134 such as, for example, teeth, so that, in this initial deployed configuration, the gripping features 134 of one of the jaws 120 contact the gripping features 134 of the other jaw 120. In particular, in the initial deployed configuration, the jaws 120 extend toward one another so that target tissue may be gripped between the jaws 120 via the gripping features 134.

However, when the clip 102 is mounted over the adapter 108 in the insertion configuration, the jaws 120 extend about opposing portions of the adapter 108 so that an exterior surface 136 of the adapter 108 maintains the clip 102 in an open configuration, with the jaws 120 separated from one another. Thus, when the clip 102 is mounted over the adapter 108, target tissue may be drawn into the space between the jaws 120. When the clip 102 is moved distally off of the adapter 108, the clip 102 is free to close under the natural bias of the hinges 128. It will be understood by those of skill in the art that the hinges 128 and/or jaws 120 of the clip 102 may be formed of any of a variety of materials so long as the hinges 128 bias the jaws 120 toward the initial deployed configuration, as described above, and so that the bias is sufficiently strong to maintain the clip 102 in clipped position over target tissue after the clip has been finally deployed. In one example, portions of the clip 102 (e.g., the hinges 128) are formed of a shape memory alloy such as, for example, Nitinol to provide and/or add to the bias toward the closed configuration.

According to an exemplary embodiment, as described above, each of the jaws 120 includes an opening 122 extending therethrough from a first surface 138 of the clip 102, which faces the adapter 108, to a second surface 140 of the clip 102, which faces away from the adapter 108. In one embodiment, the opening 122 extends through each of the jaws 120 midway between the first and the second ends 130, 132 thereof so that the openings 122 extend through opposing portions of the clip 102. Each opening 122 is sized, shaped, and configured to receive a portion of a corresponding one of the control wires 116 therein. In particular, the enlarged distal end 118 is positioned distally of the second surface 140 so that a remaining length of the control wire 116 passes proximally through the opening 122.

As discussed above, the clip 102 may be mounted to the insertion device 104, as shown in FIGS. 1-4, which may include any standard endoscope 106. The clip 102 may be mounted to the endoscope 106 via the adapter 108, which is sized, shaped, and configured to be coupled to the endoscope 106. In one embodiment, the adapter 108 is mountable over the distal end 110 of the endoscope 106 and configured to be movable relative thereto via steering members 112. The adapter 108 may be moved longitudinally relative to the endoscope 106 and/or angled with respect to the longitudinal axis of the endoscope 106 to steer the adapter 108 relative to the endoscope 106 between the first position, in which the adapter 108 is substantially aligned with the endoscope 106, and second position, in which the adapter 108 is angled and/or bent away from the longitudinal axis of the endoscope 106. As will be understood by those of skill in the art, the endoscope 106 is configured to be inserted through a body lumen to a target area within the lumen and thus, must be sufficiently flexible to navigate through even tortuous paths of the body lumen.

The adapter 108 extends from a proximal end 142 to a distal end 144 and includes a channel 146 extending therethrough. A proximal portion 143 of the adapter 108 is configured to be mountable over or otherwise couplable to the distal end 110 of the endoscope 106 while a distal portion 145 is configured to receive the clip 102 thereover in the insertion configuration. The proximal portion 143 of the adapter 108 may be mounted to the endoscope 106 via, for example, a friction fit, so that the channel 146 of the adapter 108 is substantially longitudinally aligned with a channel of the endoscope 106. Thus, tissue may be viewed through the channel 146 via an optical system of the endoscope 106. In another embodiment, to enhance a visibility of the tissue and/or the clip 102, the adapter 108 may be formed of a transparent material.

In an exemplary embodiment, the proximal portion 143 of the adapter 108 includes a pair of holes 148 extending longitudinally through a wall 150 thereof. Each of the holes 148 is configured to slidably receive a corresponding one of the extending members 114 therein. As will be described in further detail below, the extending members 114 are received within the holes 148 so that the distal ends 124 of the extending members 114 extend distally of the holes 148 toward the clip 102, which is mounted over the distal portion 145 of the adapter 108. In one embodiment, the holes 148 extend through diametrically opposing portions of the adapter 108.

An outer diameter of the distal portion of the adapter 108 is sized, shaped, and configured to receive the clip 102 thereover, in the insertion configuration. In one exemplary embodiment, the distal portion 145 tapers toward the distal end 144 so that the clip 102 is biased toward the initial deployed configuration. When the clip 102 is mounted over the distal portion 145 of the adapter 108 with each of the jaws 120 extending over opposing portions thereof, the exterior surface 136 of the adapter 108 holds the clip 102 in the insertion configuration with the jaws 120 of the clip 102 separated from one another. The clip 102 may remain mounted over the adapter 108 in the open insertion configuration so long as a sufficient proximally directed tension is applied thereto via the control wires 116. If the tension is removed from the control wires 116, a natural bias of the clip 102 draws the jaws 120 toward one another pushing the clip 102 distally over the tapered surface of the distal portion 145 of the adapter 108 until the clip 102 slides distally off of the adapter 108. In one embodiment, the control wires 116 and the extending members 114 may be moved simultaneously, in a distal direction relative to the adapter 108 and/or endoscope 106, to release a tension along the control wires 116 so that the clip 102 may be moved toward the initial deployed configuration.

In one embodiment, the distal portion 145 of the adapter 108 includes features for reducing friction between the clip 102 and the exterior surface 136 thereof to facilitate the sliding of the clip 102 therealong. For example, the distal portion 145 may include flat portions 152 distributed about a circumference thereof. In another embodiment, the distal portion 145 may also include features configured to facilitate the re-opening of the jaws 120 as the clip 102 is moved from initial deployed configuration back toward the insertion configuration. For example, the distal portion 145 may include a plurality of projections 154 extending distally from the distal end 144 of the adapter 108 at an angle relative to a longitudinal axis of the adapter 108 so that, when the clip 102 is drawn proximally from the initial deployed configuration the jaws 120 abut the projections 154 with the angle of the projections 154 facilitating the re-opening of the jaws 120, against their natural bias, toward the open insertion configuration. That is, the jaws 120 slide proximally over the projections 154 to re-open the jaws 120 so that the clip 102 is released from the clipped tissue and can be slid proximally back into the adapter 108.

Figure 6:
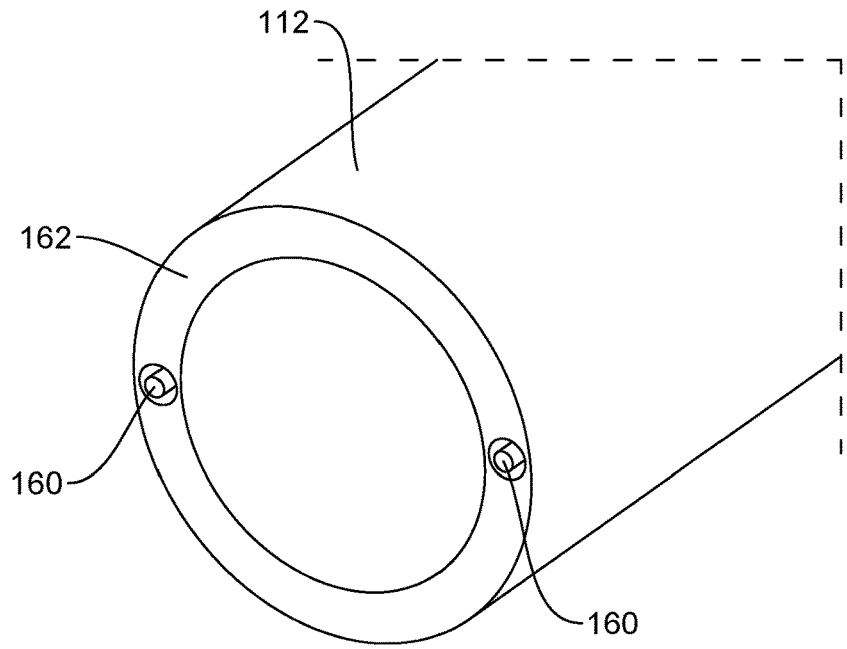
FIG. 6 shows a perspective view of a steering member according to the system of FIG. 1.

The insertion device 104 of an exemplary embodiment includes steering members 112 which extend along a length of the endoscope 106 from proximal ends 156 accessible to the user via, for example, the user interface 126, to distal ends 158 which are connected to the adapter 108. In an exemplary embodiment, as shown in FIG. 6, each of the steering members 112 of one embodiment is formed of a hollow braid of Pebax (or any other suitable material) including at least two steering wires 160 through a wall 162 thereof. Although each steering member 112 is shown and described as including two steering wires 160, it will be understood by those of skill in the art that the steering members 112 may include more than two steering wires to facilitate additional directions of motion of the adapter 108 relative to the endoscope 106. The distal ends 158 are connected to the adapter 108 so that each of the steering members 112 is substantially aligned with a corresponding one of the holes 148 extending through the wall 150 of the proximal portion 143 of the adapter 108. In particular, each of the steering members 112 of one embodiment are coaxially aligned with the corresponding one of the holes 148.

According to an exemplary embodiment, each steering member 112 extends through an outer shaft 164 extending along a length of the endoscope 106 from a proximal end 166 connected to the user interface 126 to a distal end 168. The steering members 112 are longitudinally movable relative to the outer shafts 164 to steer the adapter 108 relative to the distal end 110 of the endoscope 106 between the first and second positions. The steering members 112 extend through the outer shafts 164 so that distal ends 158 extend distally out of the shafts 164 to be connected to the adapter 108 at the distal end 110 of the endoscope 106. According to an exemplary embodiment, the outer shafts 164 extend along opposing longitudinal sides of the endoscope 106 so that the steering members 112 extend therethrough to be connected to the adapter 108, as described above. In one embodiment, the outer shafts 164 have a coil configuration to facilitate a flexing thereof as the endoscope 106 is inserted through a body lumen.

Figure 7:
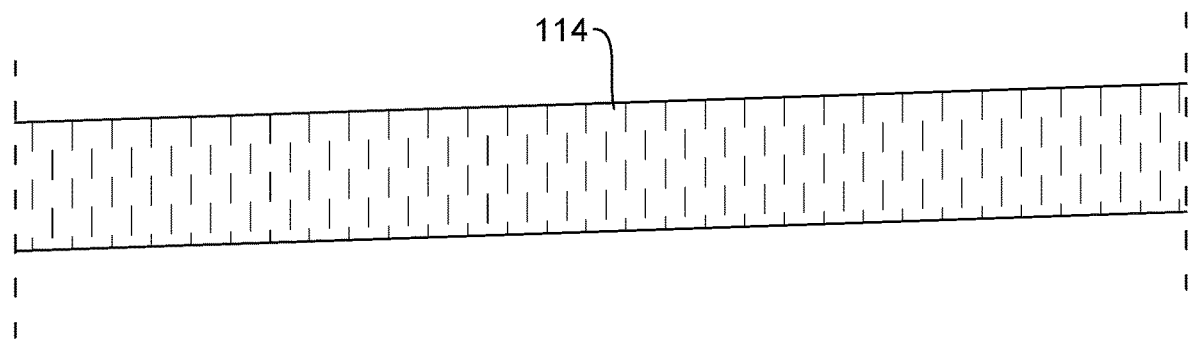
FIG. 7 shows a longitudinal side view of an extending member according to the system of FIG. 1.

Extending members 114 are slidably received within the hollow steering members 112. In this embodiment, each extending member 114 extends from a proximal end 115 connected to the user interface 126 through a corresponding one of the steering members 112 and through the corresponding one of the holes 148 so that distal ends 124 extend distally from the holes 148 toward the clip 102. In one embodiment, the extending members 114 are configured as nitinol hypotubes. In one example, as shown in FIG. 7, one or more of the nitinol hypotube includes alternating cuts thereabout to facilitate a bending thereof as the steering members 112 are bent to control a movement of the adapter 108 relative to the endoscope 106.

Figure 8:
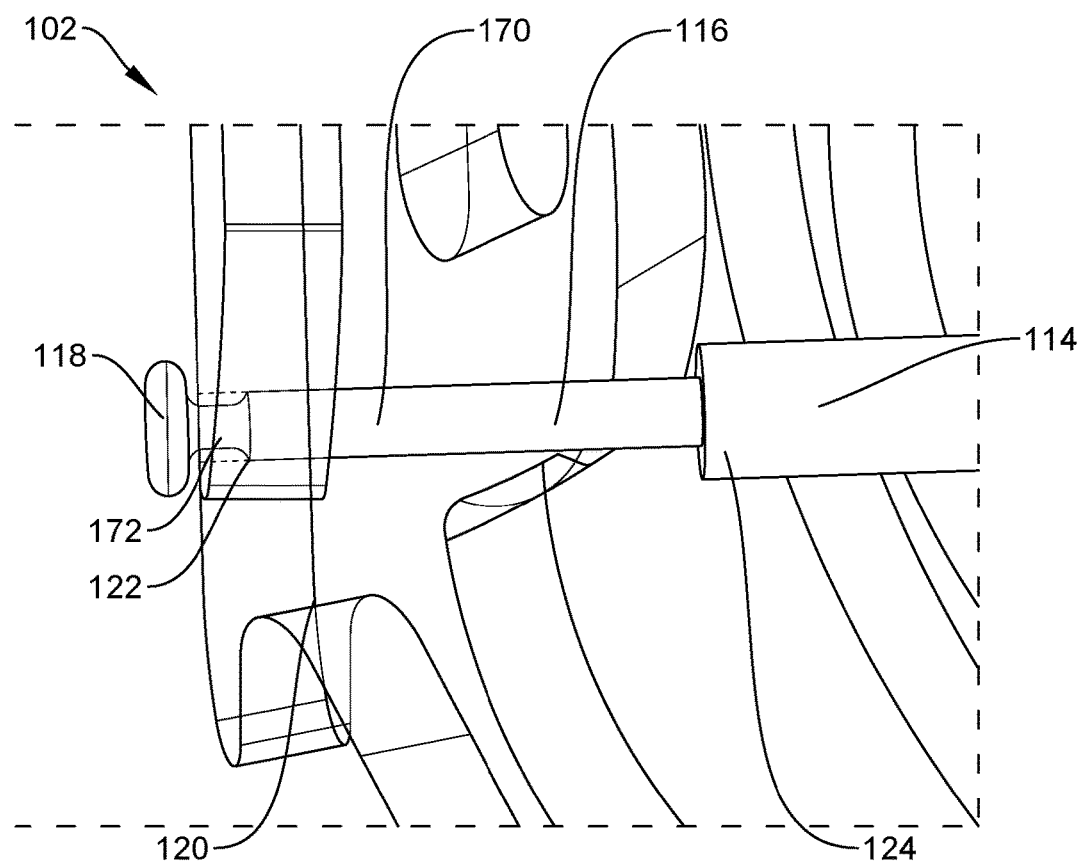
FIG. 8 shows an enlarged side view of a control wire and the extending member coupled to the clip according to the system of FIG. 1.

As shown in FIG. 8, the control wires 116 extend through the extending members 114 from proximal ends 117 connected to the user interface 126 to the enlarged distal ends 118, which extend distally of the distal ends 124 of the extending members 114. The enlarged distal ends 118 of the control wires 116 engage the second surface 140 of the clip 102 so that a remaining length of the control wires 116 extends proximally through the openings 122 of the jaws 120 and through the extending members 114 to the user interface 126. As described above, the enlarged distal ends 118 are sized, shaped, and configured so that the enlarged distal ends 118 cannot be passed proximally through the openings 122 of the jaws 120.

Similarly, the openings 122 are sized, shaped, and configured to prevent a distal passage of the distal ends 124 of the extending members 114 therethrough. Thus, the clip 102 is held between enlarged distal ends 118 of the control wires 116 and the distal ends 124 of the extending members 114. As will be described in further detail below, while the control wires 116 are slidably received within the extending members 114, the control wires 116 and the extending members 114 may be locked relative to one another so that the control wires 116 and the extending members 114 may be moved simultaneously to control a movement of the clip 102 relative to the adapter 108 between the insertion configuration, the initial deployed configuration, and the review configuration.

Each enlarged distal end 118 is connected to the remaining length 170 of the control wire 116 via a joint 172 configured to break, fail, release or otherwise separate when subject to a predetermined threshold force. In one embodiment, the joint 172 may be configured as a reduced diameter portion of the control wire 116. In another embodiment, the joint 172 may be configured as an adhesive subject to fail when subject to the predetermined force. In yet another embodiment, the joint may be configured as a releasable coupling. It will be understood by those of skill in the art, however, that the joint 172 may have any of a variety of configurations so long as the joint 172 is configured to separate the enlarged distal end 118 from the remaining length 170 when subject to the predetermined threshold force.

Figure 9:
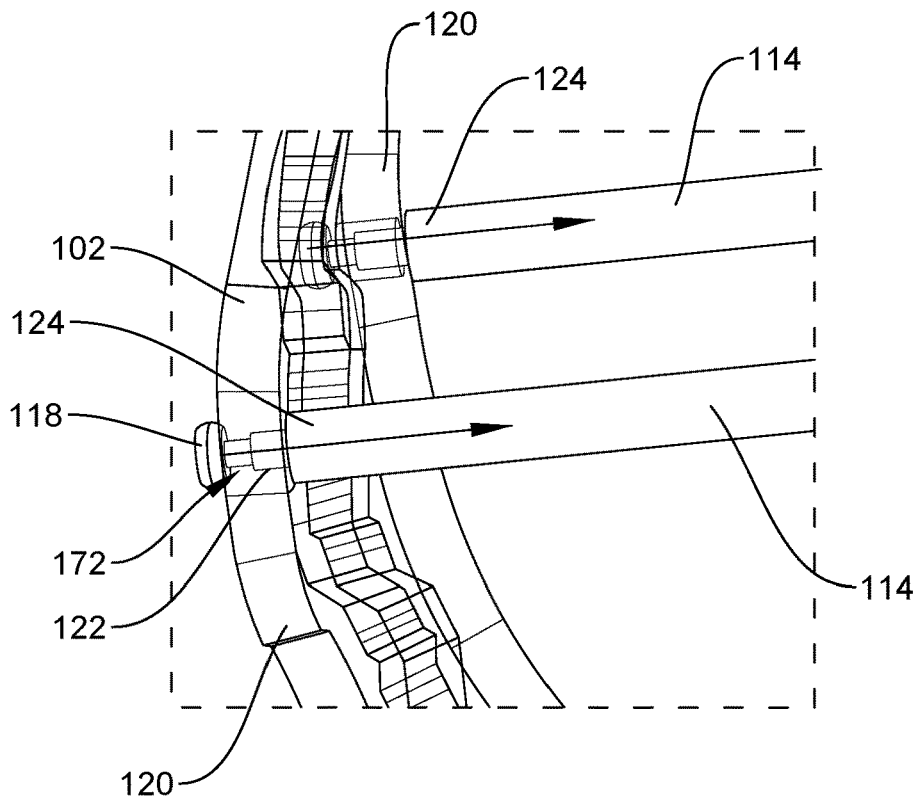
FIG. 9 shows an enlarged side view of a control wire and the extending member during a final deployment of the clip according to the system of FIG. 1.
Figure 10:
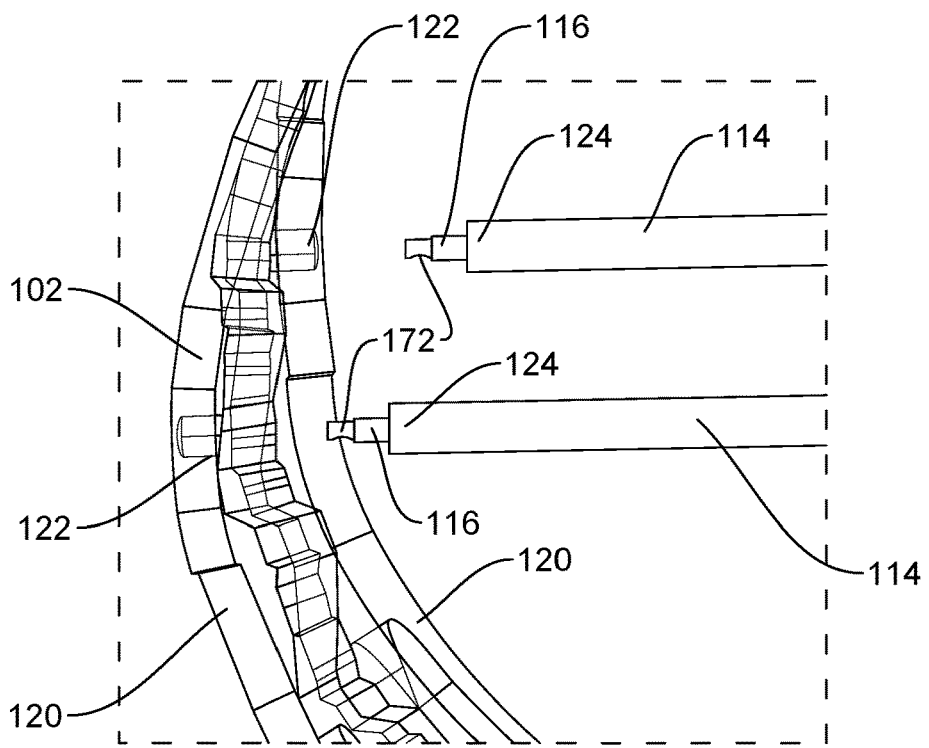
FIG. 10 shows an enlarged side view of the control wire and the extending member separated from the clip upon final deployment of the clip according to the system of FIG. 1.

Thus, when it is desired to move the clip 102 toward the final deployed configuration, the control wires 116 are drawn proximally relative to the extending members 114 so that the enlarged distal ends 118 and the clip 102 are pulled proximally against the distal ends 124 of the extending members 114, as shown in FIG. 9. The control wires 116 are pulled proximally against the extending members 114 until a force exerted on the joint 172 exceeds a predetermined threshold value so that the enlarged distal ends 118 separate from the remaining lengths 170, as shown in FIG. 10, thereby releasing the clip 102 from the insertion device 104.

According to an exemplary embodiment, as shown in FIGS. 11-13, the user interface 126 includes a handle member 174, a first actuator 176 for controlling the steering members 112, a second actuator 178 for controlling the extending members 114, and a third actuator 180 for controlling the control wires 116. In an exemplary embodiment, each of the first, second and third actuators 176, 178, 180 may be configured as knobs rotatable relative to the handle member 174, each of the knobs including a shaft 184, 186, 188, respectively, extending into the handle member 174 and about which proximal ends of the steering members 112, the extending members 114 and the control wires 116 may be coupled.

Proximal ends 156 each of the steering members 112 may be coupled to the shaft of the first actuator 176 so that when, for example, the first actuator 176 is rotated relative to the handle member 174, the first actuator 176 is moved between the first position, in which the first actuator 176 is substantially aligned relative to the longitudinal axis of the endoscope 106, and the second position, in which the first actuator 176 is angled and/or bent with respect to the longitudinal axis of the endoscope 106. Proximal ends 115 of the extending members 114 may be coupled to the shaft 186 of the second actuator 178 with proximal ends 117 of the control wires 116 coupled to the shaft 188 of the third actuator 180 so that rotation of the second and third actuators 178, 180 relative to the handle member 174 moves the extending members 114 and the control wires 116, respectively, longitudinally relative to the endoscope 106. The steering members 112, the extending members 114 and the control wires 116 may be coupled to the first, second and third actuators 176, 178, 180, respectively, in any of a variety of different ways. In the embodiment shown in FIG. 13, the steering members 112, the extending members 114 and the control wires 116 are coupled to the first, second and third actuators 176, 178, 180, respectively, via a crimp 190.

The user interface 126 may further include a locking mechanism 182 for locking the second and third actuators 178, 180 relative to one another, so that the extending members 114 and the control wires 116 may be moved simultaneously in the same direction relative to the longitudinal axis of the endoscope 106 to move the clip 102 between the insertion configuration, the initial deployed configuration, and the review configuration by rotating just one of the second and third actuators 178, 180. The locking mechanism 182 may include a friction ring, which when engaged, locks the second and third actuators 178, 180 relative to one another. In another embodiment, the locking mechanism 182 may lock the second actuator 178 relative to the handle member 174 so that, during movement of the clip 102 toward the final deployment, the third actuator 180 may be rotated relative to both the handle member 174 and the second actuator 178 to draw the control wires 116 proximally relative to the clip 102 and the extending members 114.

According to an exemplary method for tissue closure utilizing the clipping system 100, the clip 102 may be inserted through a body lumen such as, for example, the GI tract, to a target area within the body lumen via the insertion device 104 which, in one embodiment, includes the endoscope 106. As described above, in the insertion configuration, the clip 102 is mounted to the distal end 110 of the endoscope 106 via the adapter 108 so that jaws 120 are separated from one another in the insertion configuration. The clip 102 is guided to the target area via the visualization system of the endoscope and positioned over target tissue. A suction force and/or tissue graspers may be applied (e.g., through a working channel of the endoscope 106) to draw the target tissue into the channel 146 of the adapter 108. Thus, when the clip 102 is moved toward the initial deployed configuration by releasing tension along the control wires 116 (e.g., by moving the control wires 116 distally relative to the endoscope 106), the clip 102 is permitted to slide distally along the adapter 108 toward the biased closed configuration. As described above, clip 102 is held between the distal ends 118 of the control wires 116 and the distal ends 124 of the extending members 114 so that the control wires 116 and the extending members 114 may be moved simultaneously in the same direction to release the tension along the control wires 116. The clip 102 may be moved toward the initial deployed configuration via rotation of one of the second and third actuators 178, 180, which may be locked relative to one another, as described above.

It will be understood by those of skill in the art that suctioning and/or gripping of the tissue in this initial deployed configuration may obstruct an imaging/optical lens of the endoscope 106 making it difficult or impossible for a user to clearly visualize clipped tissue to determine whether desired target tissue has been properly clipped. Thus, the clip 102 may be moved toward the review configuration by drawing the endoscope 106 proximally relative to the clip 102, while the clip 102 remains engaged between the distal ends 118, 124 of the control wires 116 and the extending members 114. A distance between the adapter 108 and the clip 102 widens a field of view of the endoscope 106 so that the clip 102, and the tissue gripped thereby, may be viewed via the optical/visualization system of the endoscope 106.

In this review configuration, the user may desire to steer the adapter 108 relative to the distal end 110 of the endoscope 106 from the first position, in which the adapter 108 is substantially aligned with the endoscope 106, toward the second position, in which the adapter 108 is angled or bent away from the longitudinal axis of the endoscope 106, to further enhance a visualization of the clip 102 and/or tissue. The clip 102 and adapter 108 may be steered between the first and second positions via the first actuator 176, which controls a movement of the steering members 112, as described above. It will be understood by those of skill in the art, however, that although the adapter 108 is described and shown as being moved between the first and second positions in the review configuration, the adapter 108 may be moved between the first and second positions during any of the insertion configuration, the initial deployed configuration, and the review configuration, if so desired.

If, upon visualization, the user determines that the clip 102 requires an adjustment and/or a repositioning relative to the target tissue, the control wires 116 and the extending members 114 may together be translated proximally relative to the endoscope 106 until the clip 102 is moved proximally over the adapter 108, as described above, toward the open insertion configuration. In particular, the endoscope 106 may be moved distally relative to the control wires 116 and extending members 114, while rotating the second and/or third actuator 178, 180 relative to the handle member 174, so that the clip 102 and the adapter 108 are drawn toward one another. As the clip 102 is moved toward the open configuration, the tissue gripped thereby is released, permitting the clip 102 to be repositioned over the target tissue, as desired. The clip 102 may then once again moved toward the initial deployed configuration, and then again toward the review configuration. This process may be repeated, as necessary, until the user is able to visually confirm that the clip 102 has been clipped over the target tissue, as desired.

As discussed above, the clip 102 remains engaged between the enlarged distal end 118 of the control wires 116 and the distal ends 124 of the extending members 114 during movement of the clip 102 relative to the endoscope 106 between the insertion, initial deployed and reviewed configurations. Once the user confirms that the target tissue has been clipped as desired, the clip 102 may be moved from the review configuration toward the final deployed configuration by drawing the control wires 116 proximally relative to the extending members 114. In particular, the second and third actuators 178, 180 are unlocked so that they are movable relative to one another, and the second actuator 178 may be locked relative to the handle member 174 so that rotating the third actuator 180 moves the control wires 116 relative to both the handle member 174 and the extending members 114. The control wires 116 are drawn proximally relative to the extending members 114 until a force exerted on the joint 172 exceeds a predetermined threshold value, causing the joint 172 to fail, break or otherwise separate the enlarged distal ends 118 from remaining lengths 170 of the control wires 116. Thus, the insertion device 104, including the remaining lengths 170 of the control wires 116 and the extending members 114, may be withdrawn proximally away from the clip 102 and out of the body, leaving the clip 102 clipped over the target tissue in the final deployed configuration.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:
1. A clipping system for treating tissue, comprising:
an adapter including a proximal portion configured to be coupled to a distal end of an insertion device via steering members extending from proximal ends to distal ends, the steering members extending alongside the insertion device with distal ends of the steering members connected to the proximal end of the adapter so that moving the steering members longitudinally relative to the insertion device steers the adapter between a first position, in which the adapter is substantially aligned with a longitudinal axis of the insertion device, and a second position, in which the adapter is angled away from the longitudinal axis of the insertion device;
a clip configured to be mounted over a distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration;

a first extending member slidably received within one of the steering members so that a distal end of the first extending member extends distally toward the clip; and a first control wire slidably received within the first extending member and through an opening extending through the first jaw of the clip so that an enlarged distal end of the first control wire extends distally of the opening, the enlarged distal end of the first control wire and the distal end of the first extending member being sized, shaped and configured such that the clip is held therebetween so that a simultaneous longitudinal movement of the first control wire and the first extending member relative to the adapter moves the clip between the insertion configuration, the initial deployed configuration, and a review configuration in which the clip is physically separated from the adapter to enhance visual observation of the clip.

2. The system of claim 1, wherein the enlarged distal end of the first control wire is connected to a remaining length thereof via a joint configured to separate the enlarged distal end from the remaining length when subject to a force exceeding a predetermined threshold value.

3. The system of claim 1, wherein each of the enlarged distal end of the first control wire and the distal end of the first extending member has a cross-sectional area that is larger than a cross-sectional area of the opening of the first jaw.

4. The system of claim 1, wherein the proximal portion of the adapter includes a first hole extending longitudinally through a wall thereof to slidably receive the first extending member therein such that the distal end of the first extending member extends distally of the first hole toward the clip.

5. The system of claim 1, further comprising:

a second extending member received slidably through another one of the steering members so that a distal end of the second extending member extends distally toward the clip; and a second control wire slidably received within the second extending member and through an opening extending through the second jaw of the clip so that an enlarged distal end of the second control wire extends distally of the opening of the second jaw, the enlarged distal end of the second control wire and the distal end of the second extending member being sized, shaped and configured such that the clip is held therebetween and a simultaneous longitudinal movement of the second control wire and the second extending member relative to the adapter moves the clip between the insertion configuration, the initial deployed configuration, and the review configuration.

6. The system of claim 1, further comprising outer shafts extending alongside the insertion device from proximal ends to distal ends, each of the outer shafts configured to slidably house a corresponding one of the steering members therein.

7. The system of claim 1, wherein each of the steering members is configured as a hollow braided pebax.

8. The system of claim 1, wherein each of the steering members includes at least two steering wires extending longitudinally through a wall thereof.

9. A clipping system for treating tissue, comprising:

an endoscope extending longitudinally from a proximal end to a distal end;

an adapter including a proximal portion and a distal portion, the proximal portion configured to be mountable over the distal end of the endoscope and connected thereto via first and second steering members extending from proximal ends to distal ends, the steering members extending alongside the endoscope with distal ends of the steering members connected to the proximal end of the adapter so that moving the steering members longitudinally relative to the endoscope steers the adapter between a first position, in which the adapter is substantially aligned with a longitudinal axis of the endoscope, and a second position, in which the adapter is angled away from the longitudinal axis of the endoscope;

a clip configured to be mounted over the distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration;

first and second extending members, each of the first and second extending member extending longitudinally through a corresponding one of the first and second steering members so that distal ends of the first and second extending members extend through the proximal portion of the adapter distally toward the clip; and first and second control wires, each of the first and second control wires slidably received within a corresponding one of the first and second extending members and through an opening extending through a corresponding one of the first and second jaws of the clip so that an enlarged distal end of the first and second control wire extend distally of the openings, the enlarged distal ends of the first and second control wire and the distal ends of the first and second extending members being sized, shaped and configured such that the clip is held therebetween, and a simultaneous longitudinal movement of the first control wire and the first extending member relative to the adapter moves the clip between the insertion configuration, the initial deployed configuration, and a review configuration in which the clip is physically separated from the adapter to enhance visual observation of the clip.

10. The system of claim 9, wherein each of the enlarged distal ends of the first and second control wires is connected to a remaining length thereof via a joint configured to separate the enlarged distal ends from the remaining lengths when subject to a force exceeding a predetermined threshold value.

11. The system of claim 9, wherein the enlarged distal ends of the first and second control wires and the distal ends of the first and second extending members have a cross-sectional area that is larger than a cross-sectional area of the openings of the jaws.

12. The system of claim 9, further comprising outer shafts extending alongside an insertion device from proximal ends to distal ends, each of the outer shafts configured to slidably house a corresponding one of the steering members therein.

13. The system of claim 10, further comprising a user interface including a first actuator configured to control a longitudinal movement of the first and second steering members relative to the endoscope, a second actuator configured to control a longitudinal movement of the first and second extending members relative to the adapter, and a third actuator configured to control a longitudinal movement of the first and second control members relative to the adapter.

14. The system of claim 13, wherein the user interface further comprising a locking mechanism locking the second and third actuators relative to one another such that actuation of one of the second and third actuators simultaneously moves the first and second extending members along with the first and second control wires in the same longitudinal direction relative to the adapter.

15. The system of claim 13, wherein the user interface further comprising a locking mechanism configured to lock the second actuator relative to the endoscope so that the third actuator is actuatable to move the first and second control wires relative to the first and second extending members and the endoscope to cause the joint to separate.

* * * * *